United States Patent
Watts

(10) Patent No.: US 10,952,780 B1
(45) Date of Patent: Mar. 23, 2021

(54) METHOD OF REDUCING A FRACTURE OF THE LATERAL MALLEOLUS

(71) Applicant: Retrofix Screws, LLC, Salisbury, NC (US)

(72) Inventor: Hugh Boyd Watts, Salisbury, NC (US)

(73) Assignee: RETROFIX SCREWS, LLC, Salisbury, NC (US)

(*) Notice: Subject to any disclaimer, the term of this patent is extended or adjusted under 35 U.S.C. 154(b) by 0 days.

(21) Appl. No.: 16/913,744

(22) Filed: Jun. 26, 2020

Related U.S. Application Data

(63) Continuation-in-part of application No. 16/691,777, filed on Nov. 22, 2019, now Pat. No. 10,729,478.

(51) Int. Cl.
| | | |
|---|---|---|
| A61B 17/72 | (2006.01) | |
| A61B 17/86 | (2006.01) | |
| A61B 17/16 | (2006.01) | |
| A61B 17/17 | (2006.01) | |
| A61B 17/88 | (2006.01) | |

(Continued)

(52) U.S. Cl.
CPC ...... *A61B 17/7291* (2013.01); *A61B 17/1682* (2013.01); *A61B 17/1775* (2016.11); *A61B 17/864* (2013.01); *A61B 17/8615* (2013.01); *A61B 17/8635* (2013.01); *A61B 17/8888* (2013.01); *A61B 17/8897* (2013.01); *A61B 2017/564* (2013.01); *A61B 2017/568* (2013.01);

(Continued)

(58) Field of Classification Search
CPC .............. A61B 17/864; A61B 17/1775; A61B 17/1682; A61B 17/7291
See application file for complete search history.

(56) References Cited

U.S. PATENT DOCUMENTS

| | | |
|---|---|---|
| 9,655,661 B1 | 5/2017 | Watts |
| 2005/0107791 A1* | 5/2005 | Manderson ............ A61B 17/68 606/62 |

(Continued)

FOREIGN PATENT DOCUMENTS

| | | |
|---|---|---|
| EP | 3463105 A1 | 4/2019 |
| WO | 2009152270 A1 | 12/2009 |

(Continued)

OTHER PUBLICATIONS

European Search Report dated Nov. 26, 2020 prepared by the European Patent Office in Munich, Germany related to Application No. EP 20178053; Application No./Patent No. 20178053.3-1132.

*Primary Examiner* — Christian A Sevilla

(74) *Attorney, Agent, or Firm* — Shumaker, Loop & Kendrick, LLP

(57) ABSTRACT

A method of using a screw for reducing a malleolus bone fracture. The orthopedic screw includes a unitary shaft with screw threads on a distal end of the shaft and a head on a proximal end. An enlarged terminal end segment of the head includes a socket for receiving a tool adapted for rotating the screw into aligned fibula and malleolus bone fragments at the fracture site. First and second spaced-apart tapered transition segments are formed at a juncture of the shaft and head and a juncture of the head and an enlarged terminal end segment of the head the such that rotation of the screw provides progressively increased fracture-reducing pressure between the fibula and malleolus bone fragments as the first and second tapered transition segments drives the malleolus against the fibula.

10 Claims, 13 Drawing Sheets

(51) Int. Cl.
 *A61B 90/00* (2016.01)
 *A61B 17/56* (2006.01)
 *A61B 17/68* (2006.01)

(52) U.S. Cl.
 CPC ... *A61B 2017/681* (2013.01); *A61B 2090/376* (2016.02)

(56) References Cited

U.S. PATENT DOCUMENTS

| | | |
|---|---|---|
| 2014/0277186 A1 | 9/2014 | Granberry et al. |
| 2015/0359573 A1 | 12/2015 | Adams et al. |
| 2016/0081727 A1 | 3/2016 | Munday et al. |

FOREIGN PATENT DOCUMENTS

| | | | | |
|---|---|---|---|---|
| WO | WO-2009152270 A1 | * | 12/2009 | ......... A61B 17/7266 |
| WO | 20170147537 A1 | | 8/2017 | |
| WO | 20170210574 A1 | | 12/2017 | |

* cited by examiner

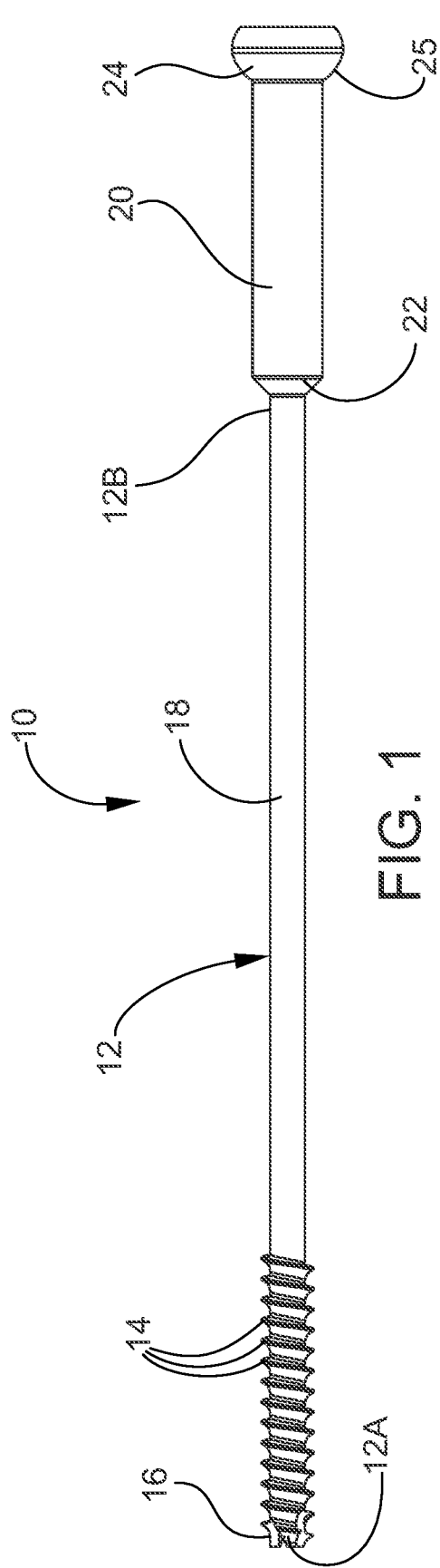
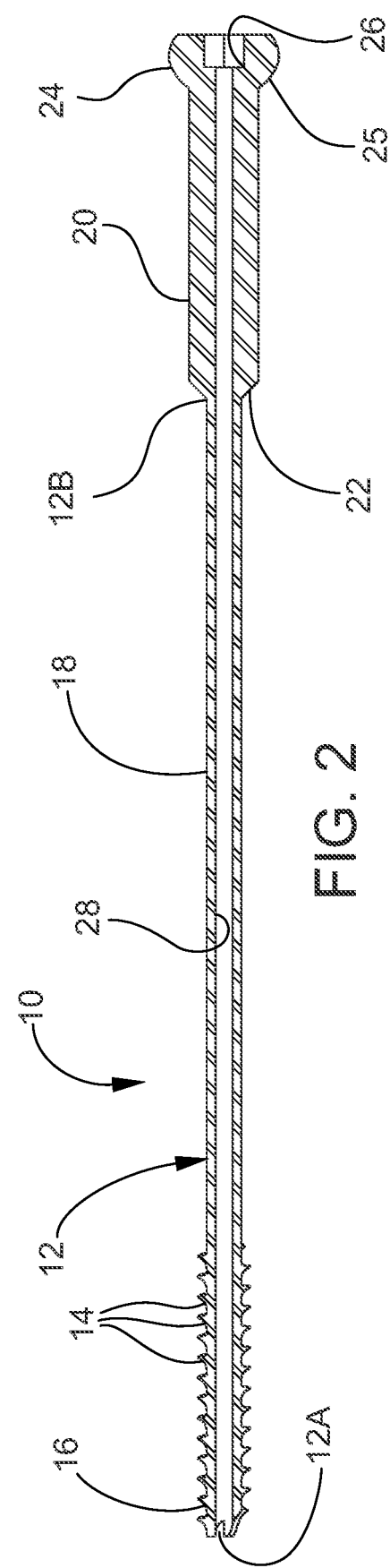
FIG. 1
FIG. 2

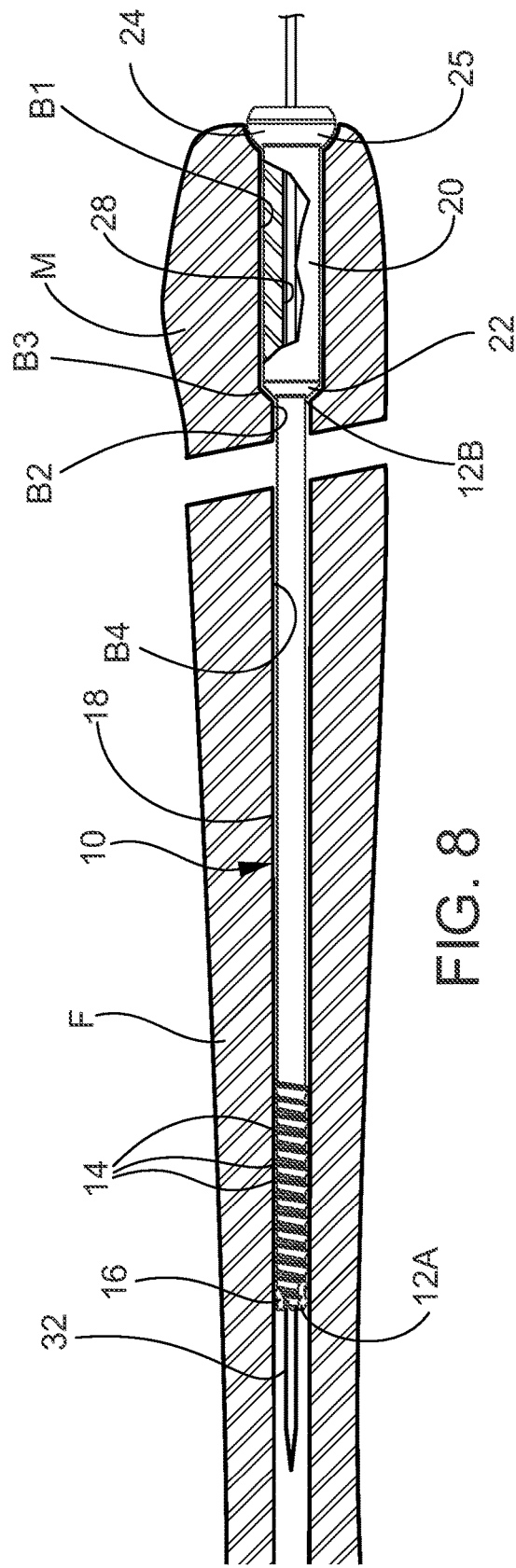
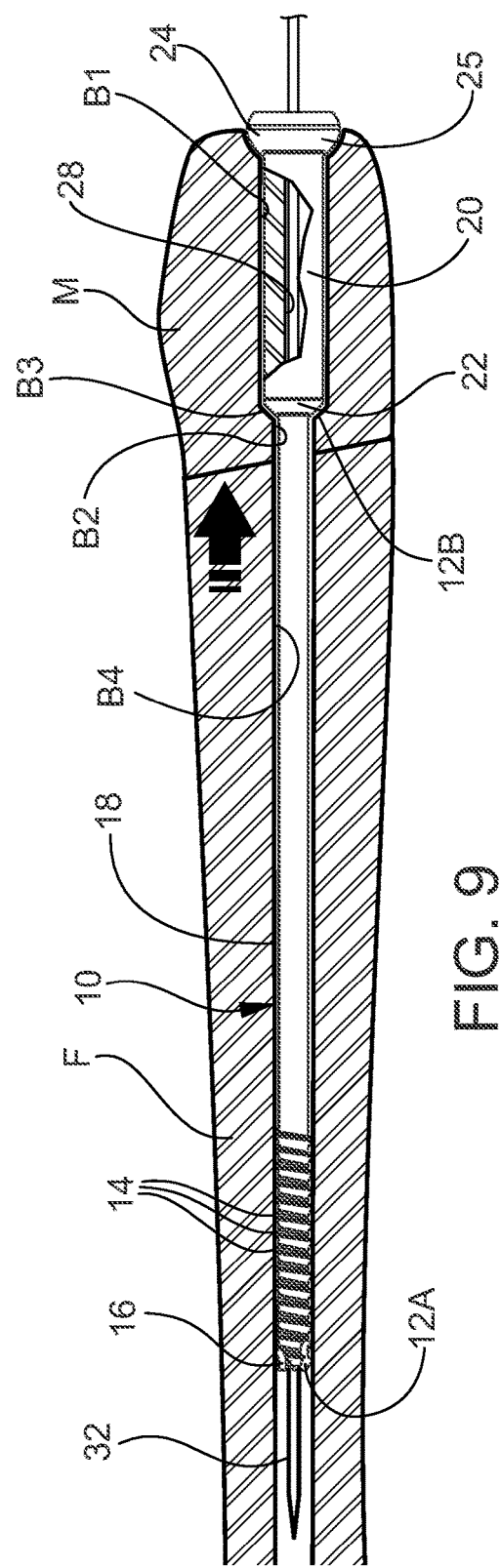
FIG. 8
FIG. 9

METHOD OF REDUCING A FRACTURE OF THE LATERAL MALLEOLUS

PRIORITY CLAIM

This application claims priority from U.S. patent application Ser. No. 16/691,777 filed Nov. 22, 2019, the contents of which are incorporated by reference in this application.

TECHNICAL FIELD AND BACKGROUND OF THE INVENTION

This invention relates to a method of using a cannulated orthopedic screw having particular application in the distal proximal fixation of lateral malleolus fractures. The ankle joint is made up of three bones coming together. The tibia, which is the main bone of the lower leg, makes up the medial, or inside, anklebone. The fibula is a smaller bone that parallels the tibia in the lower leg and makes up the lateral, or outside, anklebone. The enlarged distal ends of both the tibia and fibula are known as the malleoli (singular "malleolus"). Together, they form an arch that sits on top of the talus, one of the bones in the foot. These three bones (tibia, fibula, and talus) make up the bony elements of the ankle joint. A fibrous membrane called the joint capsule, lined with a smoother layer called the synovium, encases the joint architecture. The joint capsule contains the synovial fluid produced by the synovium. The synovial fluid allows for smooth movement of the joint surfaces. The ankle joint is stabilized by several ligaments, which hold these bones in place.

Ankle fractures occur when one or both of the malleoli are broken. These fractures are very common. Ankle fractures can happen after falls, car accidents or severe twisting of the ankle. One, two or all three malleoli can be broken. Fixation procedures for a lateral malleolus fracture have evolved over many years. Initial preferred treatment was a closed reduction of the fracture and immobilizing the malleolus with a cast or splint. Later practices have included the use of rush rods, screws and simple plates that join the fracture but without axial compression. More recent treatments have included the use of stronger and wider plates with screws or locking plates that still join the fracture but without axial compression.

Patients are instructed in non-weight bearing or minimal weight-bearing activities based on the fracture pattern, bone density, weight of the patient, mental condition and level of fixation obtained at surgery. Accurate and complete fixation in young patients is essential for good long-term results but even with accurate fixation, some patients develop non-union or articular cartilage damage and require some type of replacement later due to the cartilage damage or infection.

Older patients with osteopenia or age-related physical problems require a different approach. Most fixations of the lateral malleolus, if displaced, require open stripping of tissue from the distal fibula and plate fixation with multiple cortical and cancellous screws. A distal-to-proximal fixation of the lateral malleolus offers another way to reduce and stabilize the lateral malleolus. Such a procedure alleviates the need for open fixation, i.e., an incision and tissue retraction along the length of the ankle through which plates are mounted to the side of the bones with laterally-inserted screws. Lateral fixation with plates and screws is particularly problematic in older patients with Alzheimer's, osteoporosis, and other medical conditions. A distal-to-proximal fixation of the lateral malleolus permits a quicker fixation with a retrograde screw from the distal tip of the lateral malleolus up the medullary canal of the proximal fibula. Applicant's U.S. Pat. No. 9,655,661 discloses one advancement in lateral malleolus fixation utilizing a screw that includes screw threads along the entire length of the shaft of the screw.

The present application discloses a further improvement in with a screw that has enhanced features that permit a more accurate and robust fixation that is more resistant to displacement during healing.

SUMMARY OF THE INVENTION

It is therefore an object of the present invention to provide a method of using a cannulated orthopedic screw having particular application in the distal proximal fixation of lateral malleolus fractures.

This object and other objects and advantages of the invention are achieved by providing a method of reducing a fracture of the lateral malleolus that includes the steps of:

(a) providing an orthopedic screw for reducing a malleolus bone fracture, comprising an orthopedic screw for reducing a malleolus bone fracture, comprising a unitary shaft, including:
  (i) screw threads having a diameter and formed on a first, distal, end of the shaft, a terminal end portion of the screw threads including a sharp, biting end edge adapted to facilitate passage of the screw through a lateral malleolus and fibula of a bone at a fracture site;
  (ii) an unthreaded shank having a diameter less than the diameter of the screw threads;
  (iii) a head positioned on second, proximal end of the shaft integrally-formed to the shank and having a diameter greater than the diameter of the screw threads and the shank;
  (iv) an enlarged terminal end segment of the head including a socket for receiving a tool adapted for rotating the screw into aligned fibula and malleolus bone fragments at the fracture site;
  (v) a first tapered transition segment formed at a juncture of the shaft and head such that rotation of the screw provides progressively increased fracture-reducing pressure between the fibula and malleolus bone fragments as the first tapered transition segment drives the malleolus against the fibula; and
  (vi) a second tapered transition segment formed at a juncture of the head and enlarged terminal end segment of the head the such that rotation of the screw provides progressively increased fracture-reducing pressure between the fibula and malleolus bone fragments as the first and second tapered transition segments drives the malleolus against the fibula;

(b) determining an estimated length of both proximal and distal portions of the screw to be used;

(c) inserting an appropriate-sized drill guide until contact is made with the distal fibula;

(d) inserting an appropriate drill bit through the drill guide creating a small opening in the distal fibula;

(e) determining the length of screw by the proximal portion of the screw;

(f) removing the drill bit;

(g) inserting a wire through the drill guide and advancing the wire up the fibular canal;

(h) using anterior/posterior and lateral fluoroscopy as the wire is advanced up the fibular canal;

(i) removing the drill guide and drill bit;

(j) using a wire depth gauge to gauge the total length of the screw to be used;

(k) inserting the screw over the wire;

(l) verifying placement of the screw above the fracture site;

(m) continuing insertion of the screw until the head of the screw is countersunk into the distal fibula; and (n) confirming by anterior/posterior and lateral fluoroscopy the correct placement of the screw; and (o) removing the wire and closing the incision.

According to another aspect of the invention, the method includes the step of under drilling the opening to create added compression during screw insertion.

According to another aspect of the invention, the method includes the step of placing a sterile screw over the lateral malleolus while taking a fluoroscopic x-ray to determine appropriate screw sizing.

According to another aspect of the invention, the method includes the step of leaving the drill bit in the canal as an aid to direct the wire up the canal.

According to another aspect of the invention, the method includes the step reducing a displacement at the fracture site before the wire insertion with a bone clamp through skin of a small incision.

According to another aspect of the invention, the method includes the step of using a screw driver with a countersink reamer prior to screw insertion.

According to another aspect of the invention, the method includes the steps of:

(p) under drilling the opening to create added compression during screw insertion;

(q) placing a sterile screw over the lateral malleolus while taking a fluoroscopic x-ray to determine appropriate screw sizing;

(r) leaving the drill bit in the canal as an aid to direct the wire up the canal;

(s) reducing a displacement at the fracture site before the wire insertion with a bone clamp through skin of a small incision; and (t) using a screw driver with a countersink reamer prior to screw insertion.

According to another aspect of the invention, the method includes the steps of (a) providing an orthopedic screw for reducing a malleolus bone fracture, comprising an orthopedic screw for reducing a malleolus bone fracture, comprising a unitary shaft, including:

(i) screw threads having a diameter and formed on a first, distal end of the shaft, a terminal end portion of the screw threads including a sharp, biting end edge adapted to facilitate passage of the screw through a lateral malleolus and fibula of a bone at a fracture site;

(ii) an unthreaded shank having a diameter less than the diameter of the screw threads;

(iii) a head positioned on second, proximal end of the shaft integrally-formed to the shank and having a diameter greater than the diameter of the screw threads and the shank;

(iv) an enlarged terminal end segment of the head including a socket for receiving a tool adapted for rotating the screw into aligned fibula and malleolus bone fragments at the fracture site;

(v) a first tapered transition segment formed at a juncture of the shaft and head such that rotation of the screw provides progressively increased fracture-reducing pressure between the fibula and malleolus bone fragments as the first tapered transition segment drives the malleolus against the fibula; and (vi) a second tapered transition segment formed at a juncture of the head and enlarged terminal end segment of the head the such that rotation of the screw provides progressively increased fracture reducing pressure between the fibula and malleolus bone fragments as the first and second tapered transition segments drives the malleolus against the fibula;

(b) inserting a wire by pressure into the canal of the distal fibula to a desired depth;

(c) placing a wire depth gauge over the wire until the gauge contacts the distal fibula;

(d) determining the overall needed screw length off the end of the wire;

(e) removing the wire depth gauge;

(f) drilling the distal fibula over the wire with an appropriate-sized drill bit to the desired depth of the proximal screw portion;

(g) advancing the appropriate sized screw up the canal of the fibula over the wire with a screwdriver; and (h) removing the wire after insertion of the screw up the canal of the fibula.

According to another aspect of the invention, the method includes the steps of:

(i) making an incision in the skin below the fibula;

(j) inserting a wire through the cannula of the screw;

(k) rotating the screw with a screw driver in a direction causing the screw to be withdrawn from the canal of the fibula;

(l) removing the screw; and (m) closing the incision.

According to another aspect of the invention, the method includes the step of using a drill guide as a tissue protector.

According to another aspect of the invention, a second tapered transition segment is formed at a juncture of the head and the enlarged terminal end segment of the head the such that rotation of the screw provides progressively increased fracture reducing pressure between the fibula and malleolus bone fragments as the first and second tapered transition segments drives the malleolus against the fibula. A bore is formed in the lateral malleolus for alignment with a medullary canal of the fibula, and a screw is inserted into the bore in the lateral malleolus and the medullary canal of the fibula. The screw is rotated into the bore in the lateral malleolus and the medullary canal of the fibula into a position where the lateral malleolus and the medullary canal of the fibula are aligned in a fixed position. The screw is rotated until the second tapered transition segment bears against the malleolus. The screw is rotated until the first tapered transition segment bears against the malleolus.

According to another aspect of the invention, the method includes the steps of providing a cannula in the screw, inserting a surgical wire through the bore in the lateral malleolus and the medullary canal of the fibula wherein a length of the surgical wire remains outside the bore in the malleolus, guiding the surgical wire into the cannula of the screw, guiding the screw into the bore of the lateral malleolus and medullary canal of the fibula on the wire while rotating the screw to reduce the fracture, and removing the surgical wire from the screw by withdrawing it from the cannula of the screw.

According to another aspect of the invention, the method includes the steps of forming an incision in a foot to expose a distal end of a lateral malleolus, positioning a drill guide into the incision and abutting the exposed distal end of the lateral malleolus, inserting a drill bit having a cannula therein into the drill guide, utilizing a driver into which the drill bit is mounted to form a bore into and through the lateral malleolus and into a position proximate to and aligned with the medullary canal of the fibula. A surgical wire is inserted into the cannula of the drill bit, through the bore in the lateral malleolus and into the medullary canal of the fibula, wherein a length of the surgical wire remains outside the incision. The surgical wire is guided into the cannula of the screw and the screw is guided into the bore of the lateral malleolus and medullary canal of the fibula on the wire while rotating the screw to reduce the fracture. The surgical wire is removed by withdrawing the surgical wire from the cannula of the screw.

BRIEF DESCRIPTION OF THE DRAWING FIGURES

The present invention is best understood when the following detailed description of the invention is read with reference to the accompanying drawings, in which:

FIG. 1 is a side longitudinal elevation of an orthopedic screw in accordance with one preferred embodiment of the invention;

FIG. 2 is a side vertical cross-section of an orthopedic screw in accordance with one preferred embodiment of the invention;

FIG. 8 is a partial vertical schematic cross-section showing the position of the screw before reduction of the fracture has occurred;

FIG. 9 is a partial vertical schematic cross-section showing the position of the screw after reduction of the fracture has occurred;

FIGS. 12-25 illustrate the detailed sequence of method steps for carrying out the surgical technique involved in inserting the cannulated screw.

DETAILED DESCRIPTION OF THE PREFERRED EMBODIMENT AND BEST MODE

Figure 3:
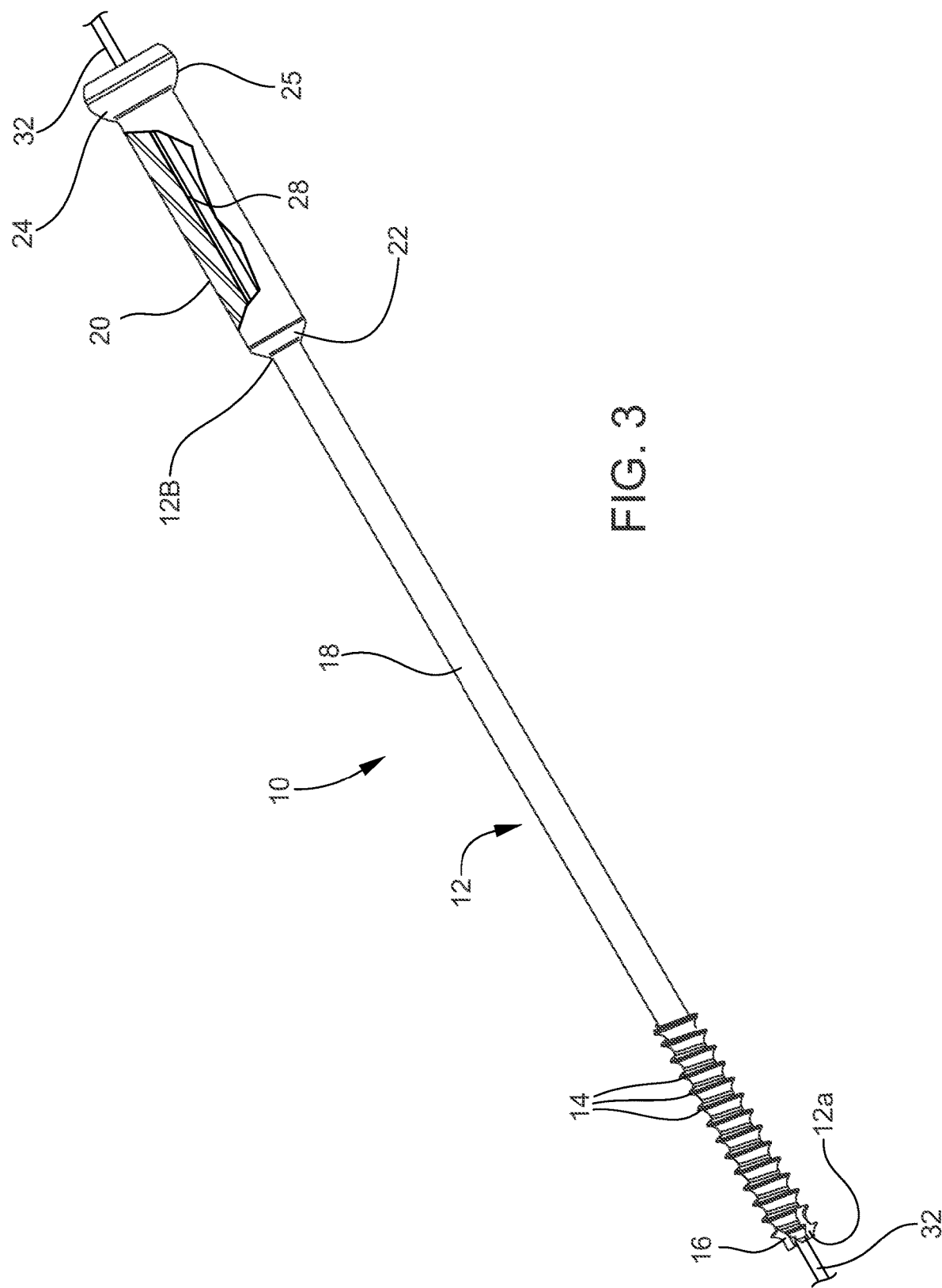
FIG. 3 is a side partial vertical cross-section of an orthopedic screw in accordance with one preferred embodiment of the invention showing a K-wire extending through the cannula of the screw.
Figure 4:
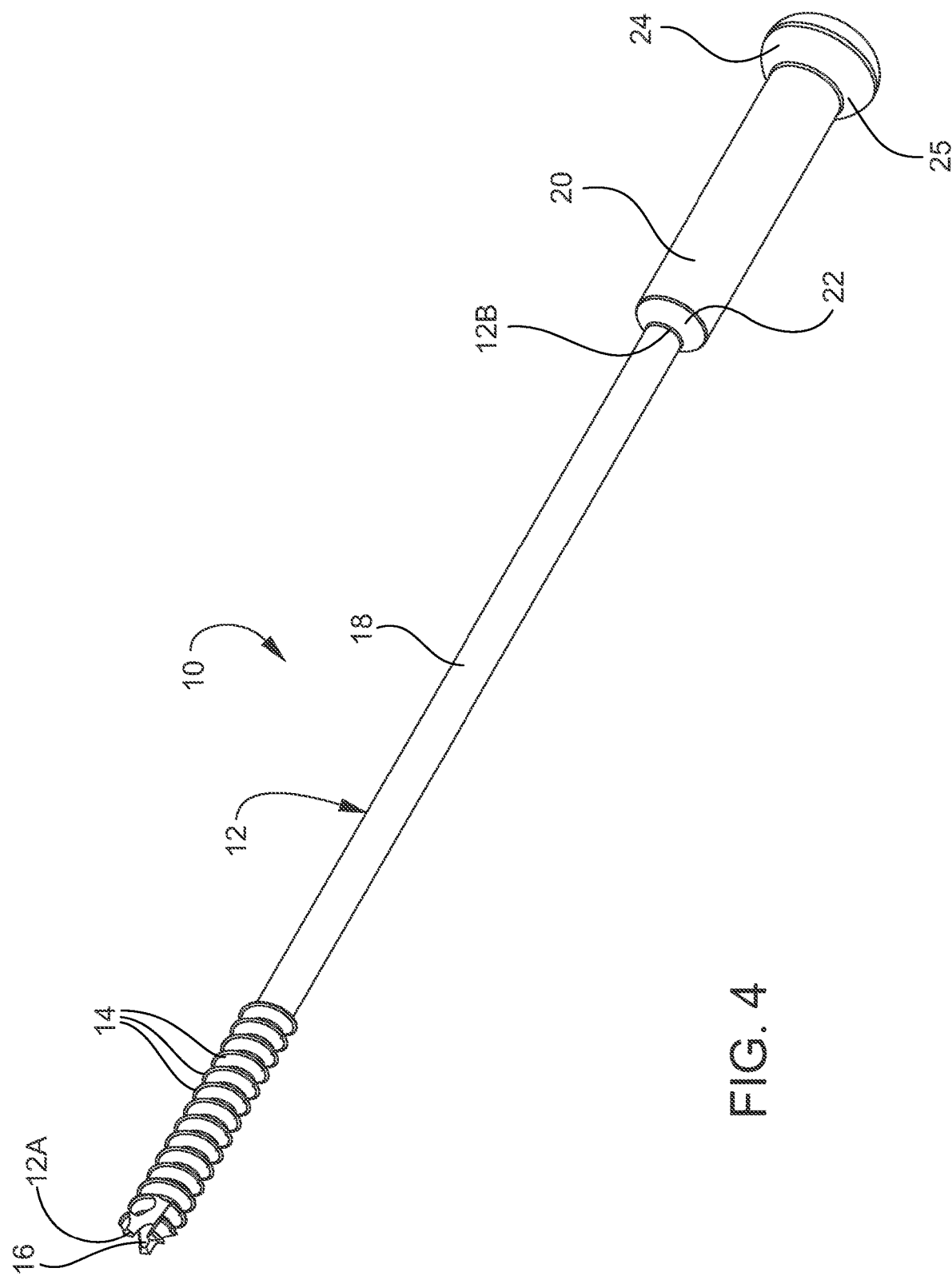
FIG. 4 is a perspective view of the screw as viewed from the threaded end of the screw.

Referring now to the drawings, an orthopedic screw used in practicing the method of the invention is shown at reference numeral 10 in the drawing Figures. Referring specifically to FIGS. 1-4, the screw 10 is fabricated of, for example, surgical grade steel, titanium, alloys thereof or other suitable materials, including suitable medical-grade coatings and/or finishes. Screw 10 includes a unitary shaft 12 with screw threads 14 formed on the shaft 12 proximate a distal first end 12A of the shaft 12. The screw threads 14 terminate at a sharp, biting end edge 16 adapted to facilitate passage of the screw 10 axially through a lateral malleolus "M" and fibula "F" (see FIGS. 8 and 9) at a fracture site.

Actual threads are 5.7 threads/cm for an HA 4.5 Screw and 6.7 threads/cm for an HA 4.0 Screw. Medical screw threads are defined as HA or HB. According to a preferred embodiment an HA 4.0 or an HA 4.5 screw thread is used, and are preferably "modified buttress threads." The modified buttress thread is used to increase compression and prevent easy pullout of the screw 10.

An unthreaded shank 18 of the shaft 12 extends to a proximate second end 12B of the shaft 12 and has a diameter less than the major diameter of the screw threads 14. A head 20 is formed on the second end 12B of the shaft 12 with a first tapered transition segment 22 formed at the juncture of the shaft 12 and an elongate enlarged head 20 such that rotation of the screw 10 provides progressively increased fracture-reducing pressure between the fibula and malleolus bone fragments as the first tapered transition segment 22 drives the malleolus against the fibula, as described in further detail below. The head 20 has a predetermined large diameter in relation to the diameter of the shaft 12.

The length of the screw threads 14 in relation to the overall length of the screw 10 is preferably approximately 19 to 31 percent. For example, for a screw 10 with a screw thread 14 length of 25 mm and a total shaft length of 130 mm, the screw threads 14 represent approximately 19 percent (25 mm/130 mm) of the total screw 10 length. For a screw 10 with a screw thread 14 length of 25 mm and a total shaft length of 80 mm, the screw threads 14 represent approximately 31 percent (25 mm/80 mm) of the total screw 10 length.

A further enlarged proximal end 24 of the head 20 includes an axially-aligned socket 26 adapted for receiving a tool, for example a hex or star tool, and for rotating the screw 10 into aligned fibula and malleolus bone fragments at the fracture site. The head 20 transitions to the proximal end 24 of the head by a second tapered transition segment 25. Rotation of the screw 10 provides progressively increased fracture-reducing pressure between the fibula and malleolus bone fragments as the second tapered transition segment 25 drives the malleolus against the fibula. Thus, both the first tapered transition segment 22 and the second tapered transition segment 25 collectively apply pressure as the screw 10 is driven into its required fixation position. This screw design provides three distinct spaced-apart points of compression along the length of the screw 10 that are capable of applying pressure required to reduce the fracture in a therapeutically appropriate manner. In situations where the fracture has a significant axial component that extends along a portion of both the malleolus and the fibula, the second tapered transition segment 25 insures that there will be pressure applied by the interaction with the screw threads 14.

A cannula 28 extends through the screw 10 from the socket 26 to the first end 12A of the shaft 12 so that a Kirshner wire, known as a "K-wire" or "surgical wire" can be passed completely through the screw 10 to act as a guide when driving the screw 10 into the aligned fibula and malleolus bone fragments.

Figure 5:
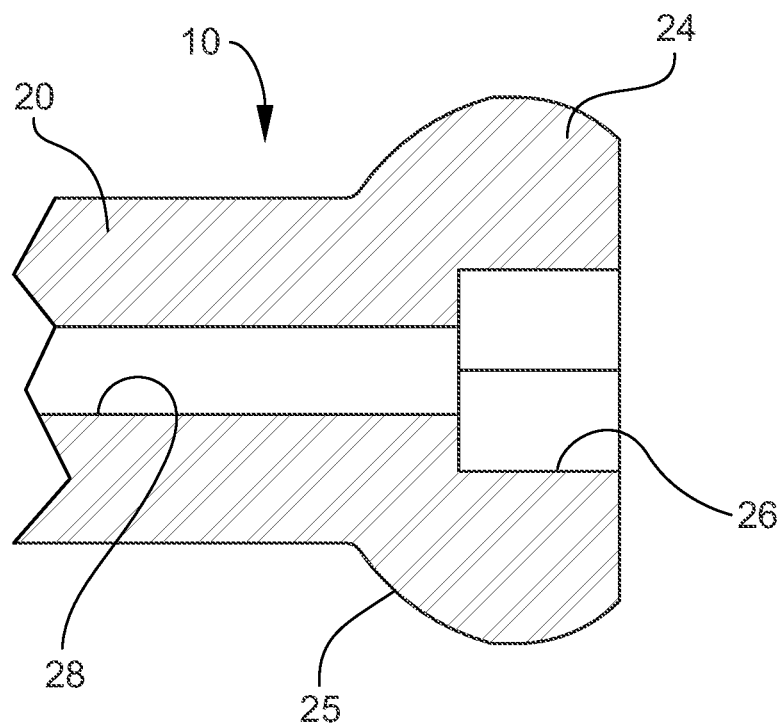
FIG. 5 is a vertical cross-section of the enlarged terminal end of the head of the screw within which the socket is located.
Figure 6:
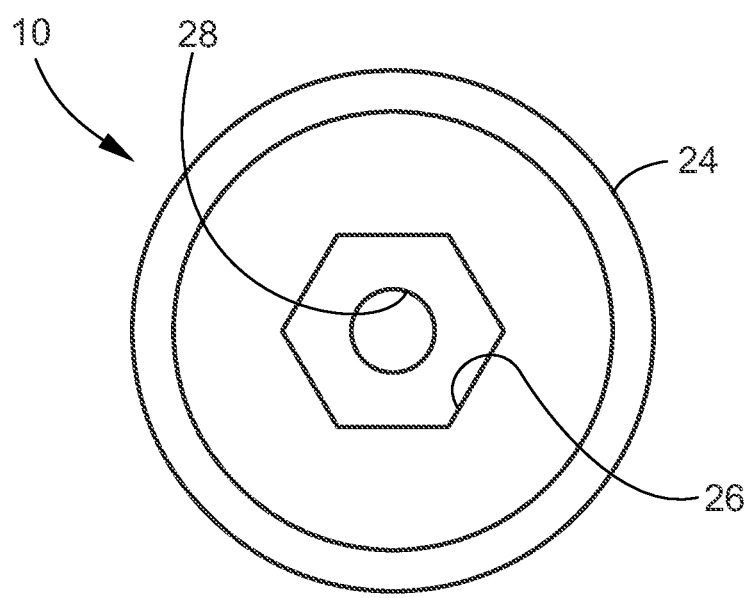
FIG. 6 is a lateral cross-section of the enlarged terminal end of the head of the screw within which the socket is located, showing a hex-configured socket.

FIGS. 5 and 6 show details of the socket 26 and the head 20.

Figure 7:
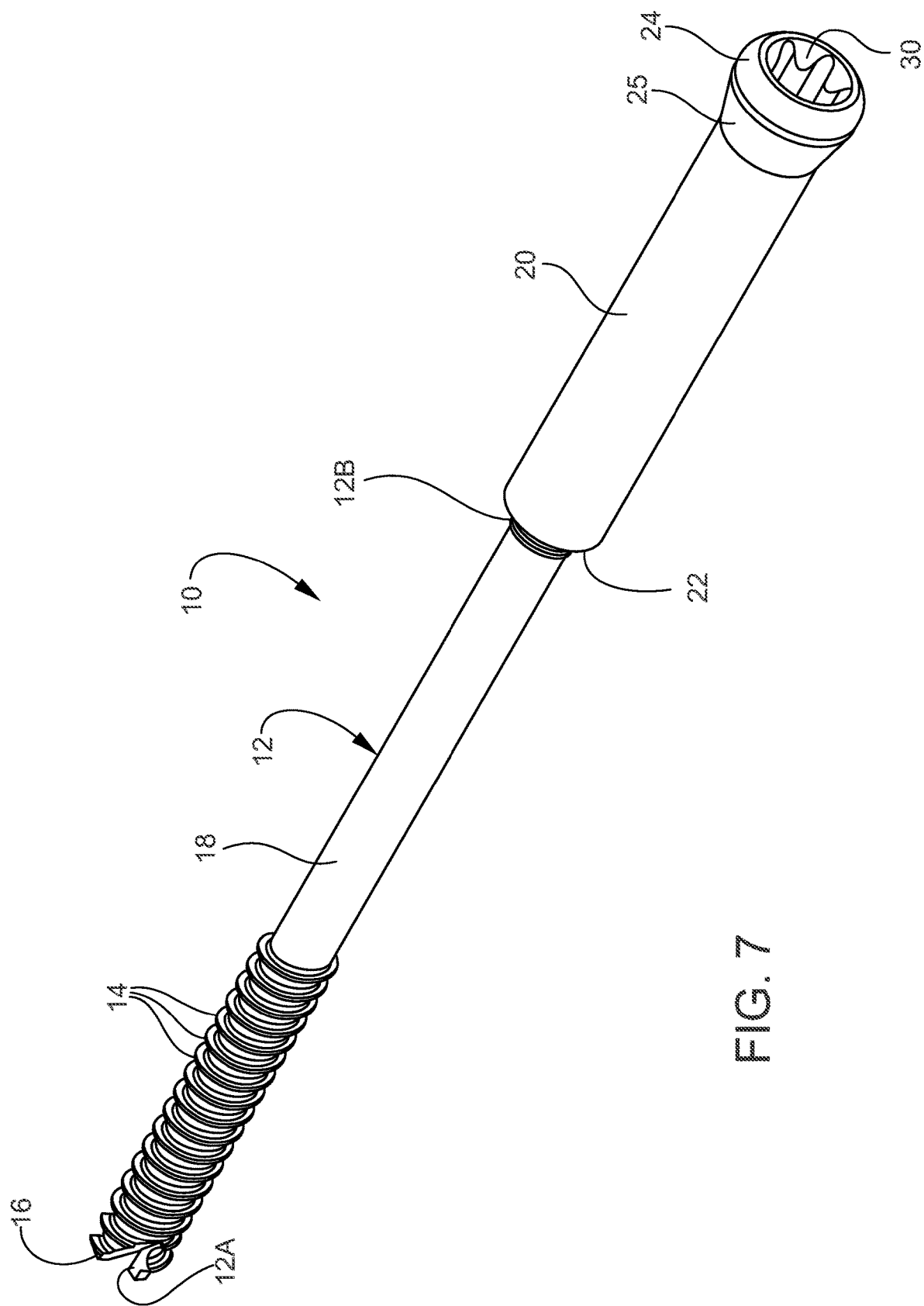
FIG. 7 is a perspective view of the screw as viewed from the head end of the screw and showing a star bit-configured socket.

FIG. 7 shows a version of the screw 10 with a socket 30 known as a "star" socket that has a 6-point star-shaped pattern that is rotated with a star bit, also referred to by its registered trademark "Torx."

Referring now to FIGS. 8 and 9, to reduce a fracture a bore is formed in the lateral malleolus "M" and the medullary canal of the fibula "F." As shown schematically, the bore in the malleolus includes a distal large diameter segment B1 and a proximal small diameter segment B2 communicating with the large diameter segment B1 and defines a radiallyinwardly extending shoulder B3. The bore in the medullary canal of the fibula F is shown at B4.

To reduce the fracture, an incision is made in the ankle to expose a distal end of a lateral malleolus. A drill guide is placed into the incision abutting the exposed distal end of the lateral malleolus. A bit having a cannula therethrough is amounted into a driver and the bit is then inserted into the drill guide in proximity to the exposed lateral malleolus. The bit is driven into and through the lateral malleolus M and into a position proximate to and aligned with the medullary canal of the fibula F forming a bore B1-B4.

A surgical wire 32 is inserted into the cannula of the bit while the bit is still positioned in the just-formed bore B1-B4 in the lateral malleolus M and the medullary canal of the fibula F. The bit is then withdrawn, leaving the surgical wire 32 in the bore B1-B4 to act as a guide for the screw 10 when inserted.

A screw 10 is selected from a range of sizes, for example, an overall length of between 80 mm to 130 mm, a head 20 diameter of 5 mm to 6 mm and a head 20 length of between 20 mm and 40 mm. The screw 10 is guided on the wire 32 into the bore B1-B4 of the fracture site.

The screw 10 is rotated into a position where the lateral malleolus M and the fibula F are aligned in a fixed position in intimate contact and the fracture is thus reduced. The threads 14 of the screw 10 facilitate cortical purchase of the screw 10 within the medullary canal of the fibula F. The relatively long unthreaded shank 18 of the shaft 12 assists in preserving adequate thickness of the surrounding bone of the fibula F and distinguishes the screw 10 from prior art screws that include threads along the entire shaft of the screw.

By continuing to rotate the screw 10 until the tapered transition segment 22 of the screw 10 bears against the shoulder B3 of the bore in the malleolus M, the fibula F and the malleolus M are drawn together into a correctly aligned reduction position. Further rotation of the screw 10 drives the first tapered transition segment 22 of the screw into a compression state against the shoulder B3 of the malleolus M. This method step also provides enhanced reduction that will improve healing by increasing blood flow between the adjacent bones at the fracture site. After the screw 10 is in its final position, the wire 32 is removed by withdrawing it from the cannula 28 of the screw 10 through the socket 26.

The above-procedures are preferably carried out using, for example, a fluoroscopy x-ray apparatus that permits the physician or technician to view in real-time the positions of the bones, drill bit, screw 10 and surgical wire 32 relative to each other, and to determine an appropriate screw size by positioning a screw 10 over the fracture site and viewing the juxtaposition of the screw in relation to the fracture.

The screw can be manufactured in a range of sizes to facilitate use on patients of varying ages, gender and body size. A typical range of sizes is set out below:

| | |
|---|---|
| Total length of screw 10 | 80-130 mm |
| Length of head 20 | 20-40 mm |
| Length of threads 14 | 25 mm |
| Diameter of enlarged terminal end 24 of the head 20 | 6.5 mm |
| Diameter of head 20 | 5-6 mm |
| Diameter of unthreaded shank 18 | 2.9-3 mm |
| Major diameter of threads 14 | 4-4.5 mm |
| Angle of first tapered transition segment 22 | 45 deg. |
| Angle of second tapered transition segment 25 | 15 deg. |

Detailed Method Sequence

Figure 10:
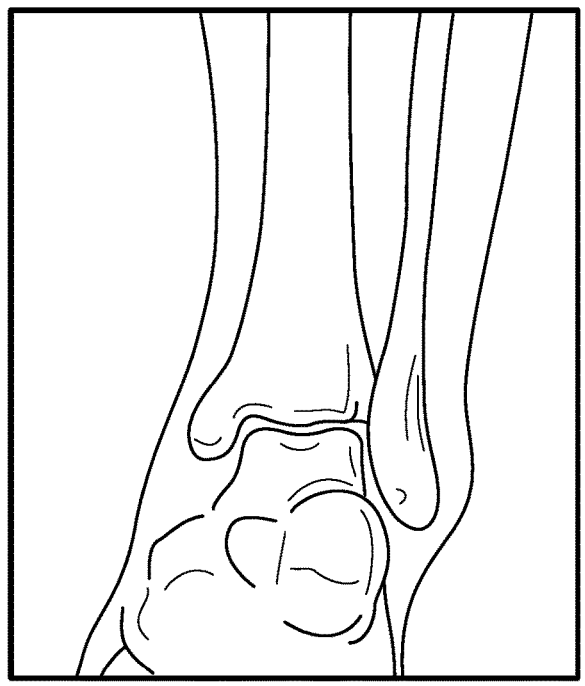
FIGS. 10-12 illustrate lateral, bi-malleolus and tri-malleolus fractures, respectively.
Figure 11:
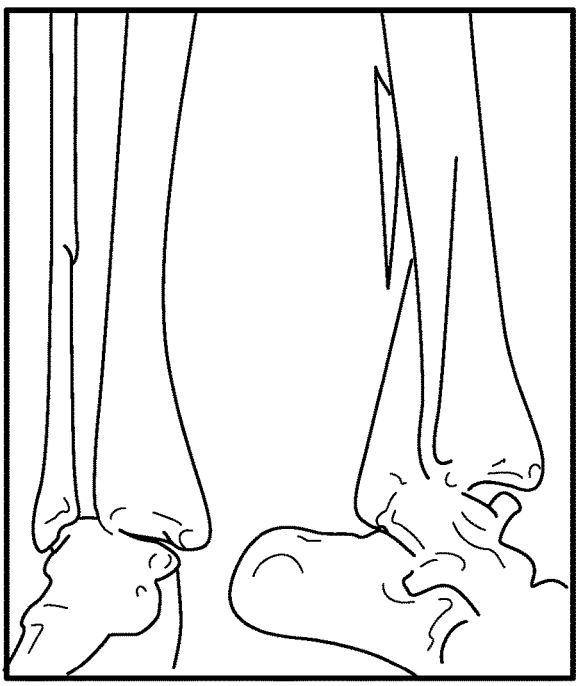
Figure 12:

As shown in FIGS. 10-12, there are various types of fractures of the malleolus, and the physician will exercise the training and experience to determine the precise manner in which the surgical use of the screw 10 occurs.

Figure 13:
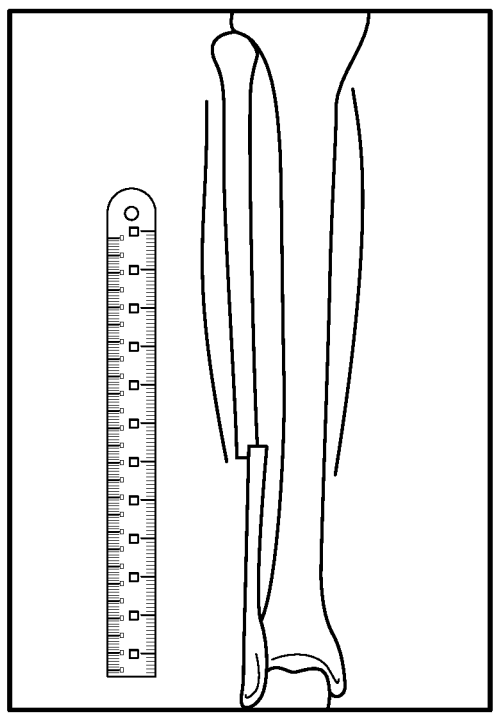

As shown in FIG. 13, a pre-op x-ray is viewed and a ruler is used to determine an estimated length of both proximal and distal portions of the screw 10 to be used. Attention should be taken to the size of the patient's canal. Typically, the 4.0 diameter screw is suitable. Under anesthesia with sterile field, a fluoroscopy unit is used to aid in the surgery. Direct surgeon visualization of the screen is recommended.

Figure 14:
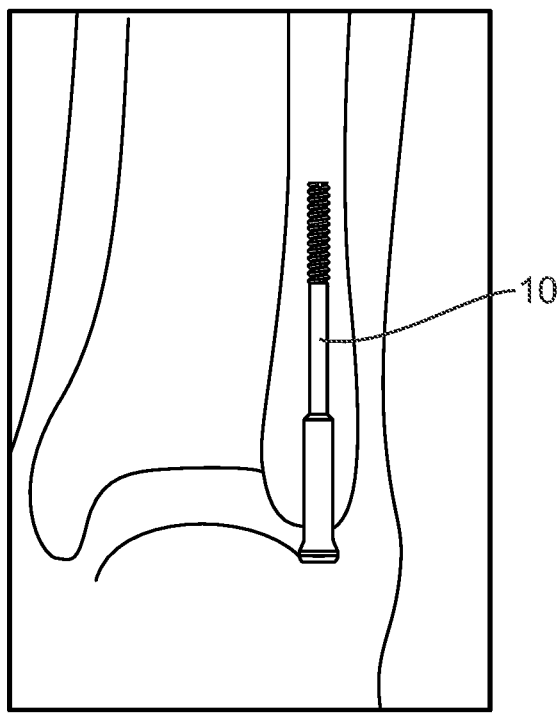

As shown in FIG. 14, (optional), a sterile screw can be placed over the lateral malleolus while taking a fluoroscopic x-ray to determine or verify appropriate screw sizing. Make a small incision as required to expose the distal tip of the fibula.

Figure 15:
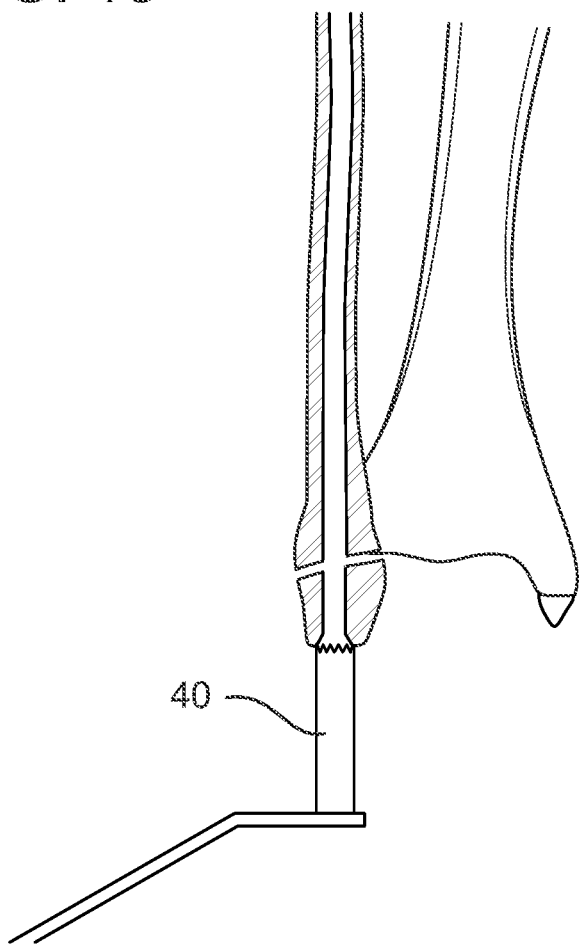

As shown in FIG. 15, with the foot inverted, insert the appropriate sized drill guide 40 until contact is made with the distal fibula. It is required to keep the guide 40 as medial as possible for adequate alignment.

Figure 16:
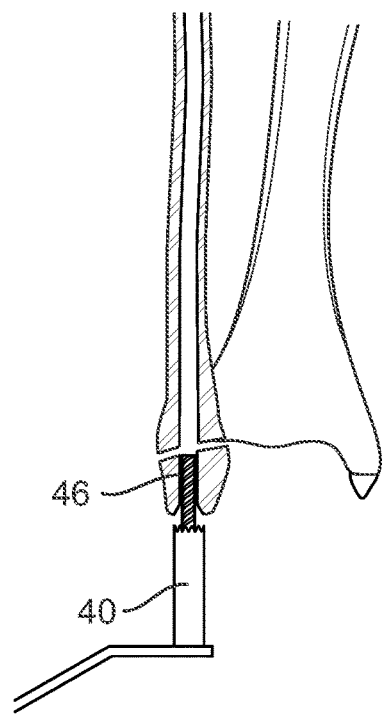

As shown in FIG. 16, insert the appropriate drill bit 46 (4.0 mm or 4.7 mm) through the drill guide 40 creating a small opening in the distal fibula. The drill bit 46 can be inserted up to but not to exceed 40 mm. This depth is determined by the proximal portion of the desired screw 10 to be used. Under drilling may help create added compression during screw insertion. If drilling to the full depth of the proximal measurement of the screw 10, this depth can be read off of the laser marking on the drill bit 46, see FIG. 18.

Figure 17:
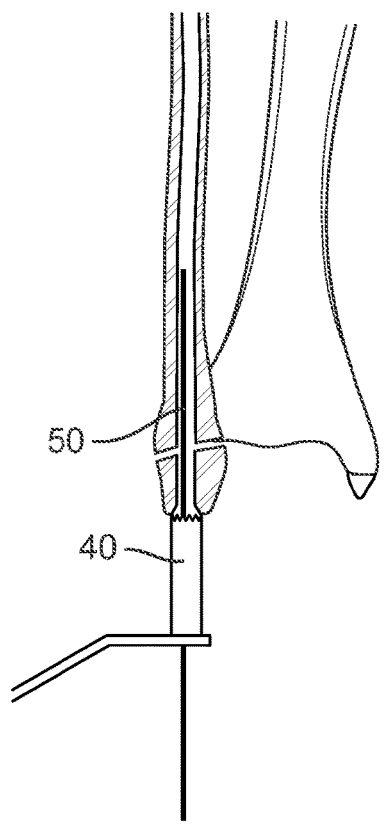

As shown in FIG. 17, remove the drill bit 46 and insert a 225×1.3 mm k-wire 50 through the drill guide 40 and up the fibular canal using low power. Utilization of anterior/posterior and lateral fluoroscopy is required as the k-wire 50 is advanced up the canal of the fibula. Depth of the k-wire 50 should be inserted to a depth at least 25 mm past the fracture to create adequate compression. Optionally, the drill bit 46 may be left in the canal at this point as an aid to direct the k-wire 50 up the canal. Using this method will require use of the 300×1.3 mm k-wire 50.

Figure 18:
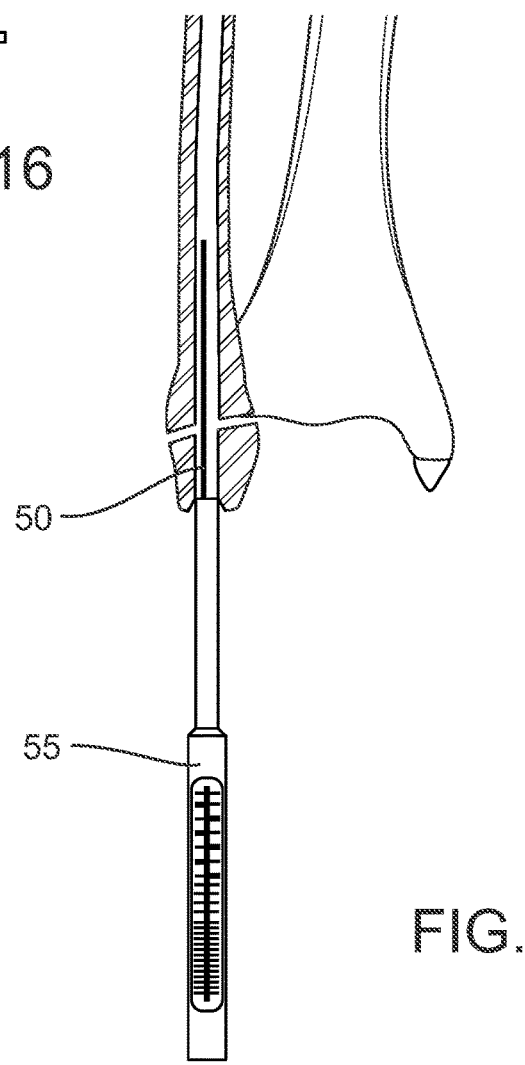

As shown in FIG. 18, remove the drill guide 50 and drill bit 46. Use a wire depth gauge 55 to gauge the total length of the screw 10 to be used. If there is some displacement at the fracture site, it can be reduced before the k-wire 50 insertion with a bone clamp through the skin of a small incision. Remove the wire depth gauge 55 and choose the appropriate screw 10 diameter based on prior measurements and preoperative planning.

Figure 19:
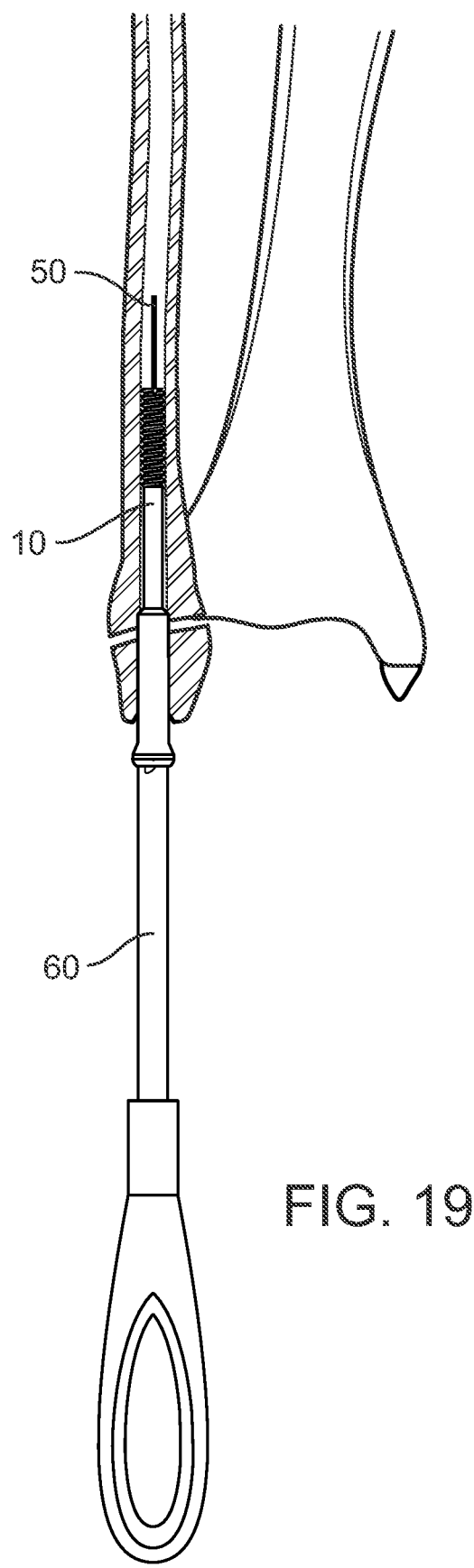

As shown in FIG. 19, insert the screw 10 over the k-wire 50 by hand with a screwdriver 60. Hand insertion helps gauge the feel and adequate purchase of the threads. Fluoroscopy should be used to verify placement of the screw 10 above the fracture site. Continue until the head of the screw 10 is countersunk into the distal fibula. In dense bone, it may be required to use the countersink reamer on the screw driver 60 prior to screw insertion.

Figure 20:
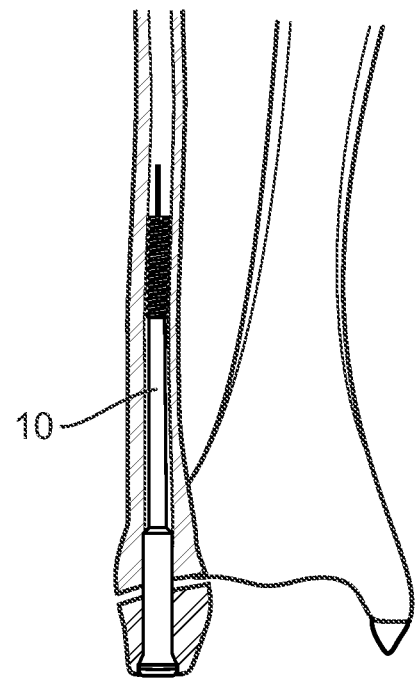

As shown in FIG. 20, confirm by anterior/posterior and lateral fluoroscopy the correct placement of the screw 10. Remove the k-wire 50 and close the incision as desired by clip, suture, or steri-strips. Post op immobilization is at the discretion of the surgeon.

Alternative Detailed Method Sequence

This advanced surgical technique can be used by discretion of the surgeon and per the patient's needs.

Figure 21:
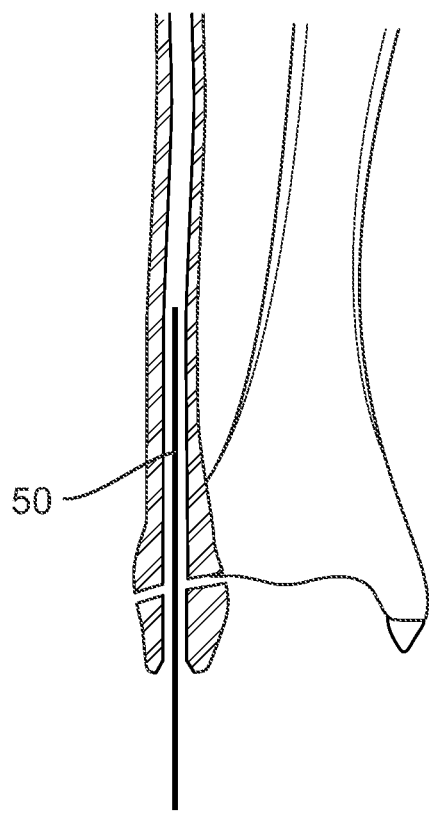

As shown in FIG. 21, insert a 225×1.3 mm k-wire 50 by pressure into the canal to the desired depth. The drill guide 40 may be used as desired as a tissue protector.

Figure 22:
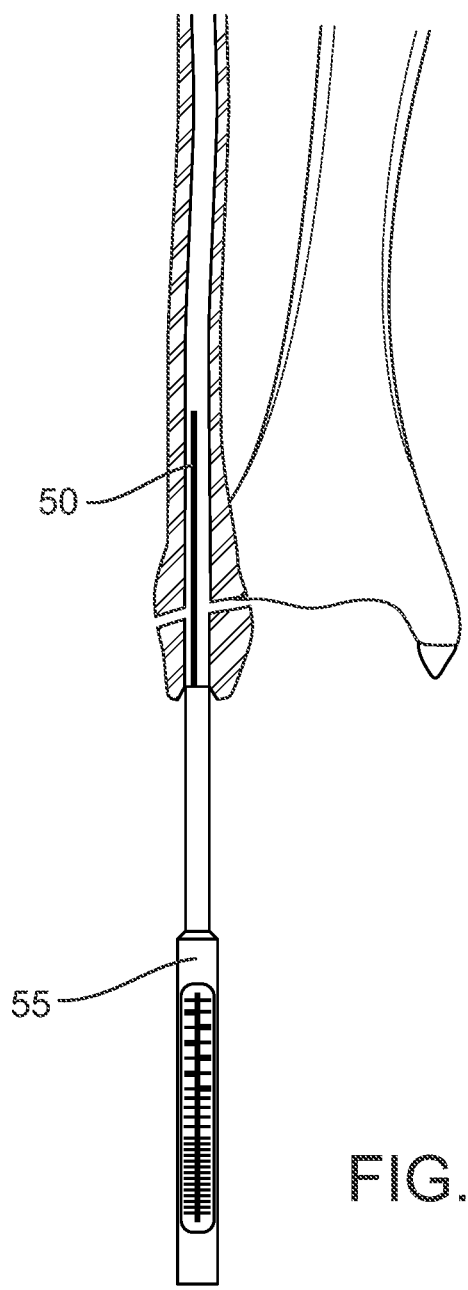

As shown in FIG. 22, place the wire depth gauge 55 over the k-wire 50 until the gauge 55 contacts the distal fibula. Overall screw length is read off the end of the k-wire 50.

Figure 23:
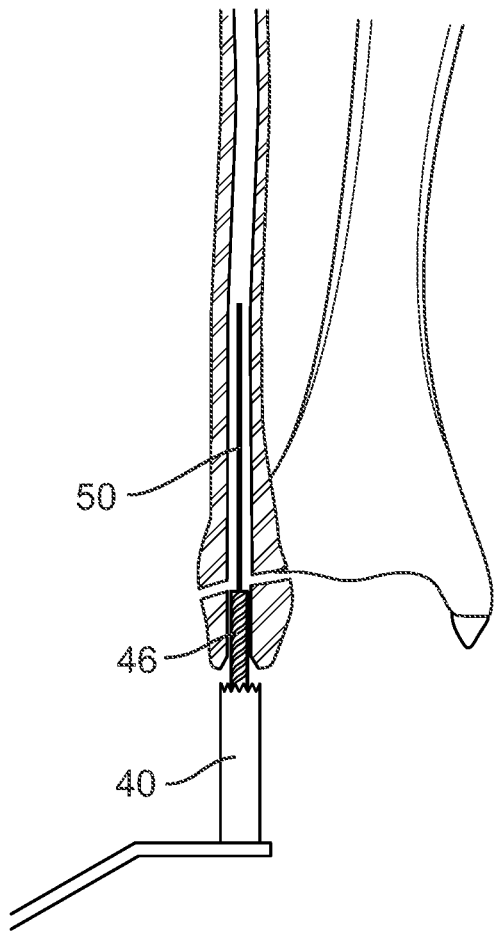

As shown in FIG. 23, remove the wire depth gauge 55 and drill the distal fibula over the k-wire 50 with the appropriate sized drill bit 46 to the desired depth of the proximal screw portion.

Figure 24:
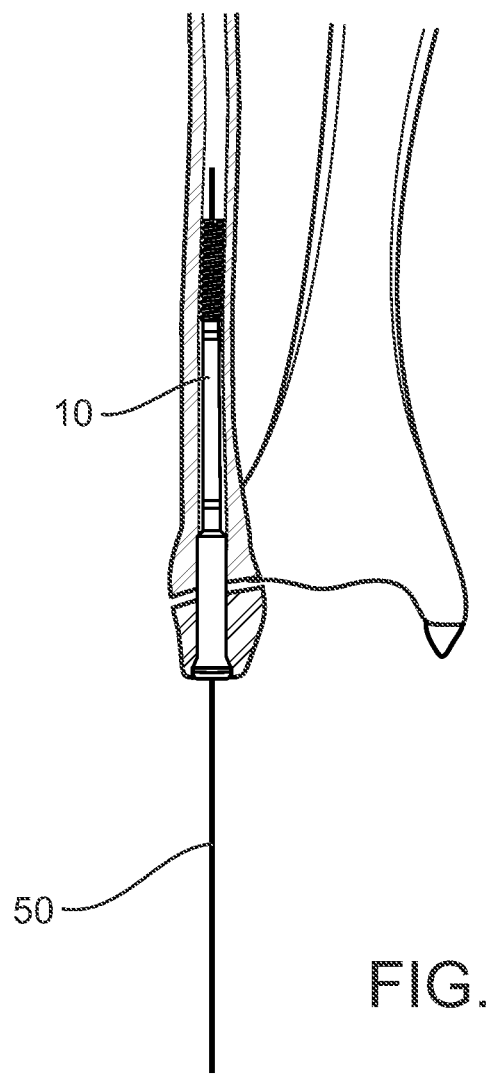

As shown in FIG. 24, advance the appropriate sized screw 10 up the canal over the k-wire 50 with the screwdriver, removing the k-wire 50 after insertion.

Figure 25:
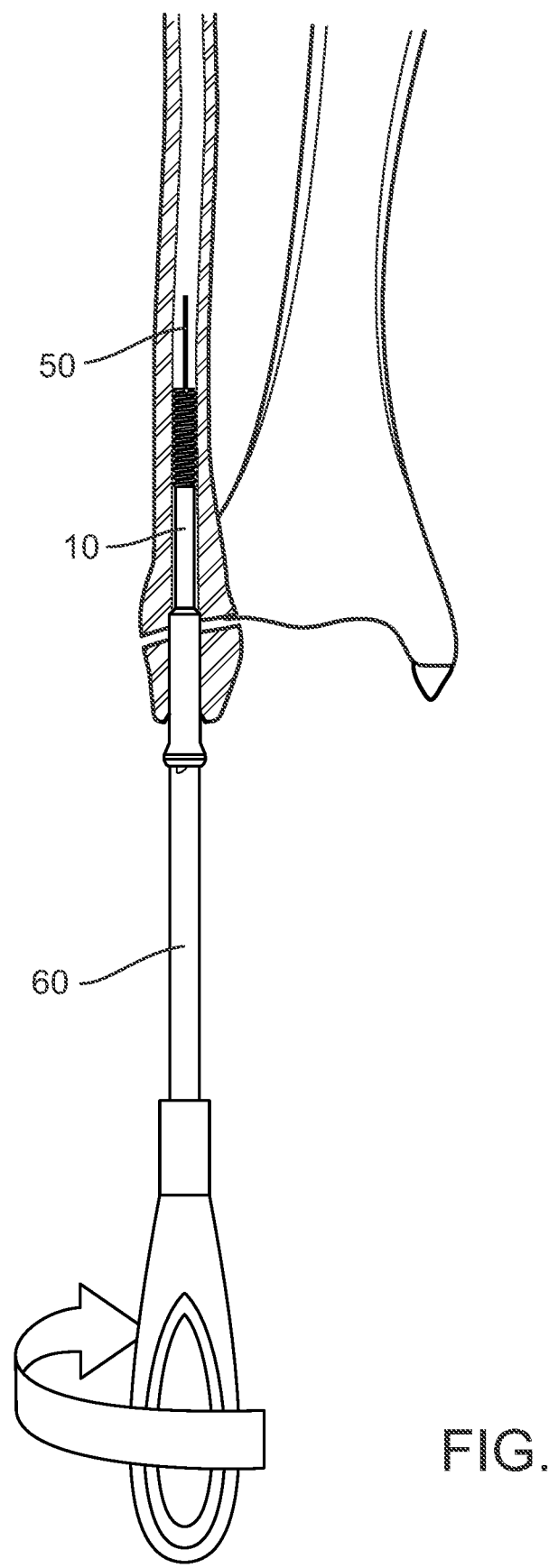

As shown in FIG. 25, should the screw need to be removed, under anesthesia make a small incision in the skin below the fibula. Insert a k-wire 50 through the screw 10 and use the screwdriver 60 to remove the screw 10 and close the incision.

While the invention has been described in relation to medical treatment of humans and specifically the reduction of a fracture of the lateral malleolus and fibula, the screw according to the disclosure of this application has applications in fracture reduction in other parts of the human body and in veterinary medical practice.

A cannulated orthopedic screw according to the invention has been described with reference to specific embodiments and examples. Various details of the invention maybe changed without departing from the scope of the invention. Furthermore, the foregoing description of the preferred embodiments of the invention and best mode for practicing the invention are provided for the purpose of illustration only and not for the purpose of limitation, the invention being defined by the claims.

I claim:

1. A method of reducing a fracture of the lateral malleolus, comprising the steps of:
   (a) providing an orthopedic screw for reducing a malleolus bone fracture comprising a unitary shaft, including:
      (i) screw threads having a diameter and formed on a first, distal end of the shaft, a terminal end portion of the screw threads including a sharp, biting end edge adapted to facilitate passage of the screw through a lateral malleolus and fibula of a bone at a fracture site;
      (ii) an unthreaded shank having a diameter less than the diameter of the screw threads;
      (iii) a head positioned on a second, proximal end of the shaft integrally-formed to the shank and having a diameter greater than the diameter of the screw threads and the shank;
      (iv) an enlarged terminal end segment of the head including a socket for receiving a tool adapted for rotating the screw into aligned fibula and malleolus bone fragments at the fracture site;
      (v) a first tapered transition segment formed at a juncture of the shaft and head such that rotation of the screw provides progressively increased fracture-reducing pressure between the fibula and malleolus bone fragments as the first tapered transition segment drives the malleolus against the fibula; and
      (vi) a second tapered transition segment formed at a juncture of the head and enlarged terminal end segment of the head the such that rotation of the screw provides progressively increased fracture-reducing pressure between the fibula and malleolus bone fragments as the first and second tapered transition segments drives the malleolus against the fibula;
   (b) determining an estimated length of both proximal and distal portions of the screw to be used;
   (c) inserting an appropriate-sized drill guide until contact is made with the distal fibula;
   (d) inserting an appropriate drill bit through the drill guide creating a small opening in the distal fibula;
   (e) determining a length of screw;
   (f) removing the drill bit;
   (g) inserting a wire through the drill guide and advancing the wire up the fibular canal;
   (h) using anterior/posterior and lateral fluoroscopy as the wire is advanced up the fibular canal;
   (i) removing the drill guide and drill bit;
   (j) using a wire depth gauge to gauge a total length of the screw to be used;
   (k) inserting the screw over the wire;
   (l) verifying placement of the screw above the fracture site;
   (m) continuing insertion of the screw until the head of the screw is countersunk into the distal fibula; and
   (n) confirming by anterior/posterior and lateral fluoroscopy correct placement of the screw; and
   (o) removing the wire and closing an incision.

2. A method according to claim 1, and including the step of under drilling the opening to create added compression during screw insertion.

3. A method according to claim 1, and including the step of placing a sterile screw over the lateral malleolus while taking a fluoroscopic x-ray to determine appropriate screw sizing.

4. A method according to claim 1, and including the step of leaving the drill bit in the canal as an aid to direct the wire up the canal.

5. A method according to claim 1, and including the step of reducing a displacement at the fracture site before the wire insertion with a bone clamp through skin of a small incision.

6. A method according to claim 1, and including the step of using a screw driver with a countersink reamer prior to screw insertion.

7. A method according to claim 1, and including the steps of:
   (p) under drilling the opening to create added compression during screw insertion;
   (q) placing a sterile screw over the lateral malleolus while taking a fluoroscopic x-ray to determine appropriate screw sizing;
   (r) leaving the drill bit in the canal as an aid to direct the wire up the canal;
   (s) reducing a displacement at the fracture site before the wire insertion with a bone clamp through skin of a small incision; and
   (t) using a screw driver with a countersink reamer prior to screw insertion.

8. A method of reducing a fracture of the lateral malleolus, comprising the steps of:
   (a) providing an orthopedic screw for reducing a malleolus bone fracture, comprising an orthopedic screw for reducing a malleolus bone fracture, comprising a unitary shaft, including:
      (i) screw threads having a diameter and formed on a first, distal end of the shaft, a terminal end portion of the screw threads including a sharp, biting end edge adapted to facilitate passage of the screw through a lateral malleolus and fibula of a bone at a fracture site;

(ii) an unthreaded shank having a diameter less than the diameter of the screw threads;

(iii) a head positioned on second, proximal end of the shaft integrally-formed to the shank and having a diameter greater than the diameter of the screw threads and the shank;

(iv) an enlarged terminal end segment of the head including a socket for receiving a tool adapted for rotating the screw into aligned fibula and malleolus bone fragments at the fracture site;

(v) a first tapered transition segment formed at a juncture of the shaft and head such that rotation of the screw provides progressively increased fracture-reducing pressure between the fibula and malleolus bone fragments as the first tapered transition segment drives the malleolus against the fibula;

(vi) a second tapered transition segment formed at a juncture of the head and enlarged terminal end segment of the head the such that rotation of the screw provides progressively increased fracture reducing pressure between the fibula and malleolus bone fragments as the first and second tapered transition segments drives the malleolus against the fibula;

(b) inserting a wire by pressure into the canal of the distal fibula to a desired depth;

(c) placing a wire depth gauge over the wire until the gauge contacts the distal fibula;

(d) determining the overall needed screw length off the end of the wire;

(e) removing the wire depth gauge;

(f) drilling the distal fibula over the wire with an appropriate-sized drill bit to the desired depth of the proximal screw portion;

(g) advancing the appropriate sized screw up the canal of the fibula over the wire with a screwdriver; and (h) removing the wire after insertion of the screw up the canal of the fibula.

9. A method according to claim 8, and including the steps of:

(i) making an incision in the skin below the fibula;

(j) inserting a wire through cannula of the screw;

(k) rotating the screw with the screw driver in a direction causing the screw to be withdrawn from the canal of the fibula;

(l) removing the screw; and (m) closing the incision.

10. A method according to claim 8, and including the step of using a drill guide as a tissue protector.

* * * * *